(12) United States Patent
Ladd et al.

(10) Patent No.: US 11,759,125 B2
(45) Date of Patent: Sep. 19, 2023

(54) WEARABLE POSTURE MONITORING DEVICE AND METHOD THEREOF

(71) Applicant: Caterpillar Inc., Deerfield, IL (US)

(72) Inventors: Beth Ladd, Seymour, IL (US); Donald L Bergh, Chicago, IL (US); Kimberly Moon, Bolingbrook, IL (US); Loay Abusalah, Oak Brook, IL (US); Alexandria Rodriguez, Chicago, IL (US); Amaan Baiyat, Chicago, IL (US); Leah Smith, Libertyville, IL (US); Michael Diaz, Chicago, IL (US); Randy De Leon, Cicero, IL (US); Alyssa Nicole Lee, Oak Lawn, IL (US)

(73) Assignee: Caterpillar Inc., Peoria, IL (US)

( * ) Notice: Subject to any disclaimer, the term of this patent is extended or adjusted under 35 U.S.C. 154(b) by 1007 days.

(21) Appl. No.: 16/409,799

(22) Filed: May 11, 2019

(65) Prior Publication Data

US 2020/0352476 A1    Nov. 12, 2020

(51) Int. Cl.
*A61B 5/11* (2006.01)
*A61B 5/00* (2006.01)
(Continued)

(52) U.S. Cl.
CPC ............ *A61B 5/1116* (2013.01); *A61B 5/486* (2013.01); *A61B 5/6804* (2013.01);
(Continued)

(58) Field of Classification Search
CPC ..... A61B 5/1116; A61B 5/486; A61B 5/6804; A61B 5/7246; A61B 5/742; A61B 5/7455; A61B 5/746; A61B 2562/164; A61B 5/7264; A61B 5/6823; A61B 5/6831; A61B 5/4561; G06F 3/14; G08B 7/06; G08B 21/18; G09B 5/02; G09B 5/065;
(Continued)

(56) References Cited

U.S. PATENT DOCUMENTS

| 4,007,733 | A | | 2/1977 | Celeste et al. |
| 6,487,906 | B1 | * | 12/2002 | Hock .................. A61B 5/6831 |
| | | | | 73/379.01 |

(Continued)

FOREIGN PATENT DOCUMENTS

| WO | 2017137852 | | 8/2017 |
| WO | 2017155423 | A1 | 9/2017 |

*Primary Examiner* — Ryan W Sherwin

(57) ABSTRACT

A wearable posture monitoring device is provided. The device includes a first posture sensor to measure a first bend parameter associated with shoulders of a user and a second posture sensor to measure a second bend parameter associated with vertebral column of the user. The device includes a control unit operatively coupled to the first posture sensor and the second posture sensor and is configured to compare the first bend parameter with a first predefined reference value and the second bend parameter with a second predefined reference value to detect an improper bend in one or more of the shoulders and vertebral column of the user. The control unit is further configured to display a visual indication, on a display interface associated with the posture monitoring device, to indicate the detected improper bend of one or more of the shoulders and vertebral column of the user.

9 Claims, 8 Drawing Sheets

(51) Int. Cl.
  *G06F 3/14* (2006.01)
  *G08B 7/06* (2006.01)
  *G08B 21/18* (2006.01)
  *G09B 5/02* (2006.01)
  *G09B 5/06* (2006.01)
  *G09B 19/00* (2006.01)
  *A41D 3/00* (2006.01)
  *A41D 27/10* (2006.01)

(52) U.S. Cl.
  CPC ............ *A61B 5/7246* (2013.01); *A61B 5/742* (2013.01); *A61B 5/746* (2013.01); *A61B 5/7455* (2013.01); *G06F 3/14* (2013.01); *G08B 7/06* (2013.01); *G08B 21/18* (2013.01); *G09B 5/02* (2013.01); *G09B 5/065* (2013.01); *G09B 19/00* (2013.01); *A41D 3/00* (2013.01); *A41D 27/10* (2013.01); *A41D 2200/20* (2013.01); *A41D 2600/20* (2013.01); *A61B 2562/164* (2013.01)

(58) Field of Classification Search
  CPC .......... G09B 19/00; A41D 3/00; A41D 27/10; A41D 2200/20; A41D 2600/20; A63B 21/4007; A63B 23/0244; A63B 2071/0655; A63B 2220/13; A63B 2220/836; A63B 2225/20; A63B 2225/50
  See application file for complete search history.

(56) References Cited

U.S. PATENT DOCUMENTS

| | | | |
|---|---|---|---|
| 8,217,797 | B2 | 7/2012 | Ikoyan |
| 9,282,893 | B2 | 3/2016 | Longinotti-Buitoni et al. |
| 9,883,703 | B2 | 2/2018 | Schultz |
| 2010/0324457 | A1 | 12/2010 | Bean et al. |
| 2011/0067253 | A1* | 3/2011 | Happel ............ A63B 23/0244 33/512 |
| 2014/0070957 | A1* | 3/2014 | Longinotti-Buitoni .................... A61B 5/02055 340/870.01 |
| 2015/0038881 | A1 | 2/2015 | Gokhale et al. |
| 2015/0065919 | A1 | 3/2015 | Cuevas et al. |
| 2016/0110986 | A1 | 4/2016 | Rosenblood |
| 2016/0262688 | A1 | 9/2016 | Nichols |
| 2017/0079562 | A1* | 3/2017 | Chang .................. A61B 5/4561 |
| 2018/0028109 | A1* | 2/2018 | Tesnow .................. A61B 5/742 |
| 2018/0098732 | A1 | 4/2018 | Williamson et al. |
| 2018/0228403 | A1* | 8/2018 | Li ........................ A61B 5/7405 |

* cited by examiner

WEARABLE POSTURE MONITORING DEVICE AND METHOD THEREOF

TECHNICAL FIELD

The present disclosure relates generally to a posture monitoring device, and more particularly to a wearable posture monitoring device and a method thereof.

BACKGROUND

Maintaining a correct posture, such as while standing, sitting, bending, etc., is one of the necessary requirements for having a healthy life. Specifically, for jobs that require a lot of physical work, such as for construction workers, maintaining a correct posture while working becomes even more important. Poor or improper posture during the day leads to issues like fatigue, which further results in reduced efficiency and productivity. Back posture training devices have been known to help people correct their back postures. Generally, such devices place sensors on the vertebral column of a user and provide feedback, such as a tactile feedback, to the user whenever an improper bend in the vertebral column is detected.

For example, U.S. Pat. No. 8,217,797 (hereinafter referred to as the '797 patent) provides sensory indication modules intimately associated with a surface for detection of angle relative to true vertical and acceleration and include feedback indicators for communicating localized information in relation to the detected angle and acceleration. Further the '797 patent provides a control module for communicating command and control instructions with the sensory indication modules.

SUMMARY OF THE INVENTION

In one aspect, a wearable posture monitoring device is provided. The device includes a first posture sensor to measure a first bend parameter associated with shoulders of a user and a second posture sensor to measure a second bend parameter associated with vertebral column of the user. The device includes a control unit operatively coupled to the first posture sensor and the second posture sensor and is configured to compare the first bend parameter with a first predefined reference value and the second bend parameter with a second predefined reference value to detect an improper bend in one or more of the shoulders and vertebral column of the user. The control unit is further configured to display a visual indication, on a display interface associated with the posture monitoring device, to indicate the detected improper bend of one or more of the shoulders and vertebral column of the user.

In another aspect, a method for monitoring posture of a user is provided. The user wears a wearable posture monitoring device having a first posture sensor positioned on the shoulders of the user and a second posture sensor positioned on the vertebral column of the user. The wearable posture monitoring device includes a control unit operatively coupled to the first and the second posture sensor. The method includes receiving, by the control unit using the first posture sensor and the second posture sensor, a first bend parameter associated with the shoulder of a user and a second bend parameter associated with the vertebral column of the user. The method further includes comparing, by the control unit, the first bend parameter with a first predefined reference value and the second bend parameter with a second predefined reference value to detect an improper bend in one or more of the shoulders and vertebral column of the user and displaying, on a display interface associated with the posture monitoring device, a visual indication indicating the detected improper bend of the one or more of the shoulders and vertebral column of the user.

In a yet another aspect, a system for monitoring a posture of a user is provided. The system includes a wearable harness and an I/O unit having a display interface operatively coupled to the wearable harness. The wearable harness includes a first shoulder strap having a first flex sensor for being positioned on a left shoulder of the user and a second shoulder strap having a second flex sensor for being positioned on a right shoulder of the user. The first and the second flex sensors are configured to measure a first bend parameter associated with the shoulders of the user. The harness further includes a back strap having at least one stretch sensor for being positioned on vertebral column of the user. The stretch sensor is configured to measure a second bend parameter associated with the vertebral column of the user. The harness further includes a control unit operatively coupled to the first and the second flex sensors and the at least one stretch sensor. The control unit is configured to compare the first bend parameter with a first predefined reference value and the second bend parameter with a second predefined reference value to detect an improper bend in one or more of the shoulders and vertebral column of the user. The control unit is further configured to display a visual indication, on the display interface of the I/O unit, to indicate the detected improper bend of the one or more of the shoulders and vertebral column of the user.

DETAILED DESCRIPTION

Reference will now be made in detail to specific embodiments or features of the present disclosure, examples of which are illustrated in the accompanying drawings. Generally, corresponding reference numbers will be used throughout the drawings to refer to the same or corresponding parts. Also, wherever possible, the same reference numbers will be used throughout the drawings to refer to the same, or the like parts.

Figure 1:
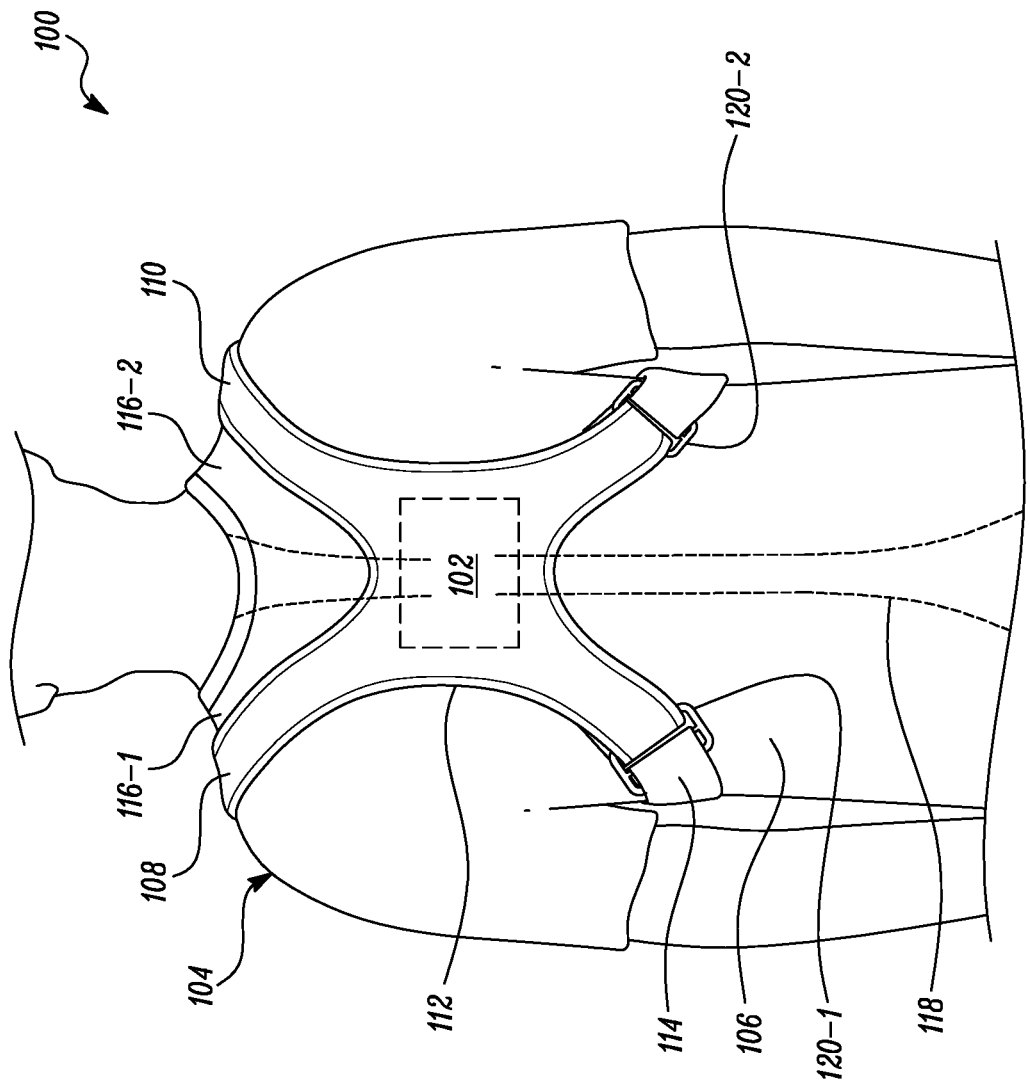
FIG. 1 illustrates an exemplary wearable harness having a wearable posture monitoring device, in accordance with an embodiment of the present disclosure.

FIG. 1 illustrates an exemplary wearable harness 100 (hereinafter referred to as the harness 100) having a wearable posture monitoring device 102, according to various embodiments of the present disclosure. In one example, the harness 100 and the wearable posture monitoring device 102 are configured to be worn by a user 104 on the chest (not shown) and the back 106. In various implementations, the harness 100 may be a detachable or an integral part of an apparel like a jacket, vest, shirt or any other top garment.

As shown in FIG. 1, the harness 100 includes a first shoulder strap 108, a second shoulder strap 110, a back strap 112 and a waist strap 114 that facilitate the user 104 in wearing the harness 100. The first shoulder strap 108 and the second shoulder strap 110 are configured to be positioned on the shoulders 116 of the user 104, whereas the back strap 112 is provided in between the first and the second shoulder strap 108, 110 and configured to be positioned on the vertebral column 118 of the user 104. Similarly, the waist strap 114 is configured to be positioned on the waist of the user 104 and facilitate locking (not shown) of the harness 100 when the user 104 wears it. The first and the second shoulder straps 108, 110 and the waist strap 114 may be adjustable using adjusters 120 to accommodate different sized users while maintaining appropriate positioning of the harness 100 on the back 106 of the user 104.

It may be contemplated that the design of the harness 100 having the wearable posture monitoring device 102 is merely exemplary and is not to be construed in a limiting manner. The wearable harness 100 along with the posture monitoring device 102 may be altered suitably to be worn in any other manner to achieve similar results, without deviating from the scope of the claimed subject matter.

Figure 2:
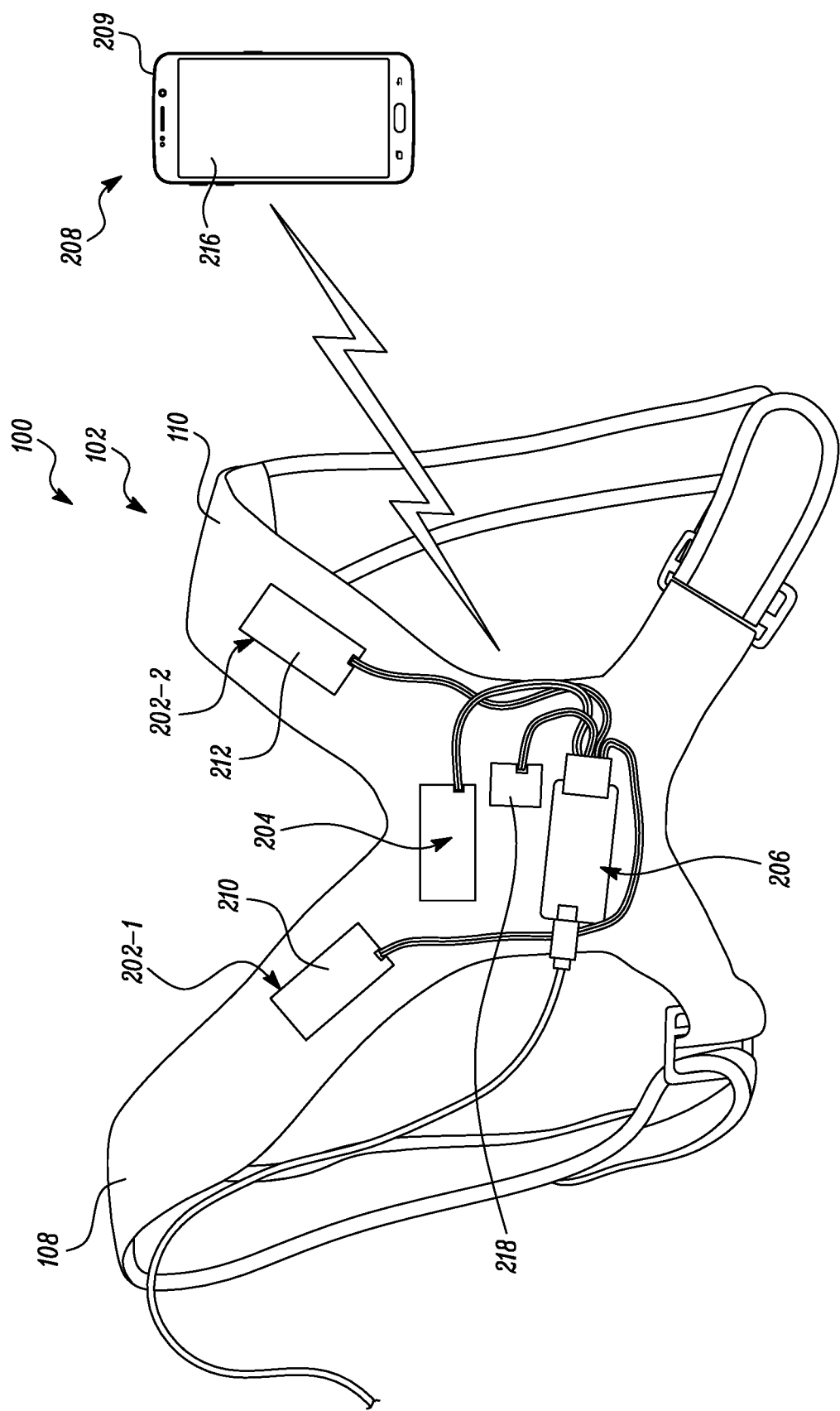
FIG. 2 illustrates various components of the exemplary wearable posture monitoring device, in accordance with the embodiment of the present disclosure.
Figure 3:
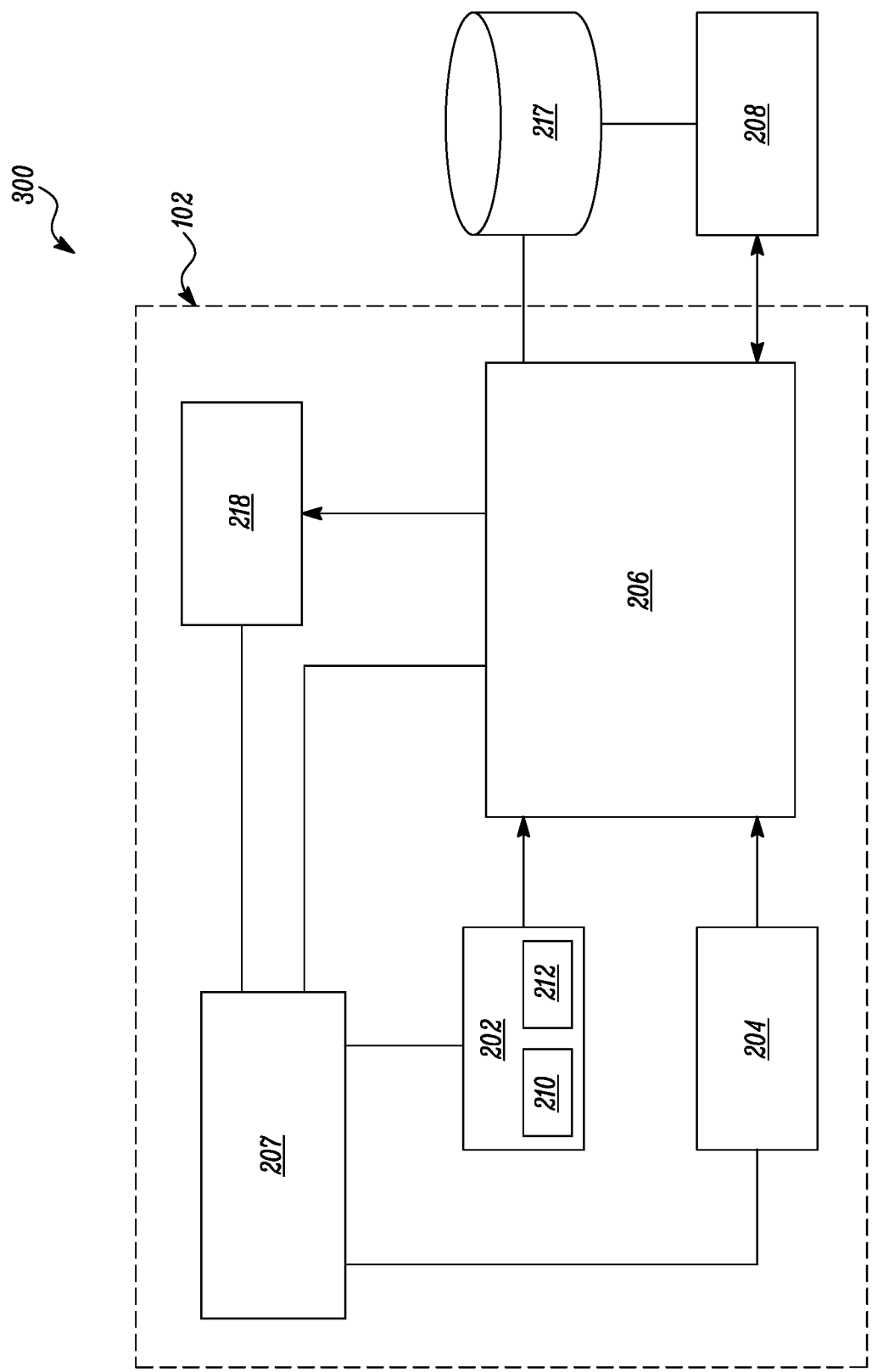
FIG. 3 illustrates a block diagram of an exemplary system for monitoring posture of a user, in accordance with an embodiment of the present disclosure.

FIG. 2 illustrates the various components of the exemplary wearable posture monitoring device 102 and FIG. 3 illustrates a block diagram of a system 300 for monitoring the posture of the user 104 using the wearable harness 100 and the wearable posture monitoring device 102. Referring collectively to FIGS. 2 and 3, the wearable posture monitoring device 102 includes at least one first posture sensor 202, at least one second posture sensor 204, and a control unit 206 operatively coupled to the at least one first posture sensor 202 and the at least one second posture sensor 204. In an embodiment of the present disclosure, the system 300 includes an input/output unit 208 (hereinafter referred to as the I/O unit 208) associated with the posture monitoring device 102 and communicatively coupled to the control unit 206. The various components of the posture monitoring device 102, including the sensors 202, 204, and the control unit 206 may be powered by a power source 207 positioned thereon. The power source 207 may be implemented as a standard rechargeable battery, such as a lithium ion battery, nickel-cadmium battery, lead-acid battery or the like.

In an exemplary embodiment, the at least one first posture sensor 202 may include one or more flex sensors positioned on the shoulders 116 to determine a bend and curvature of the shoulders 116. Further, the at least one second posture sensor 204 may include one or more stretch sensors positioned on the vertebral column 118 of the user 104 to determine a posture of the vertebral column 118. Although the first posture sensor 202 and the second posture sensor 204 are shown and described to be flex sensors and stretch sensors, respectively, it may be contemplated that any other types of sensors may also be used to achieve the similar results, without deviating from the scope of the claimed subject matter.

The control unit 206 may be implemented as a standard microcontroller (known in the art) mounted on the harness 100 and configured to communicate with the first posture sensor 202, the second posture sensor 204, the I/O unit 208 and other components (described in the following paragraphs of the description) of the system 300. In an exemplary embodiment of the present disclosure, the control unit 206 is configured to monitor posture of the user 104 and detect any improper posture. The control unit 206 may be further configured to communicate wirelessly with the I/O unit 208, such as via Bluetooth®, to display posture related information and/or information related to the detected improper posture of the user 104. The detailed functionalities and operations of the control unit 206 are further explained in greater detail in the following paragraphs of the description.

The I/O unit 208 may embody, for example, a laptop, a handheld device, or any other device capable of receiving inputs from a user and providing information output to the user. The I/O unit 208 is further capable of communicating with the control unit 206. In the illustrated embodiment, the I/O unit 208 is provided remotely with respect to the control unit 206 and the posture monitoring device 102. However, it may be contemplated that in certain implementations, the I/O unit 208 may be provided integrated with the wearable posture monitoring device 102 and the harness 100. In an exemplary embodiment of the present disclosure, the I/O unit 208 is a mobile device 209 having its own processor and being capable of wirelessly communicating with the control unit 206, such as via Bluetooth®. Other modes of wireless communication between the I/O unit 208 and the control unit 206 may also be contemplated without deviating from the scope of the claimed subject matter. It may be contemplated that the processor (not shown) of the mobile device 209 may cooperate with the control unit 206 to perform the functionalities provided in the following paragraphs of the description. Alternatively, the control unit 206 may be configured to solely perform all the functionalities, without deviating from the scope of the claimed subject matter.

In an embodiment of the present disclosure, the first posture sensor 202 includes a first flex sensor 210 and a second flex sensor 212 configured to monitor a first bend parameter associated with the shoulders 116 of the user 104. The first bend parameter indicates the bend and curvature in the shoulders 116 of the user 104. In an example implementation, the first flex sensor 210 is positioned on the first shoulder strap 108 of the harness 100 whereas the second flex sensor 212 is positioned on the second shoulder strap 110 of the harness 100. Accordingly, the first flex sensor 210 is configured to be positioned on the left shoulder 116-1 and the second flex sensor 212 is configured to be positioned on the right shoulder 116-2 of the user 104. Each of the first flex sensor 210 and the second flex sensor 212 is configured to measure a bend on each of the left and the right shoulders 116 to determine the first bend parameter indicating the bend and curvature in the shoulders 116 of the user 104. The flex sensors 210, 212 are commonly known in the art and hence the description of working of the flex sensors to determine the bend in the shoulders 116 is not provided herein for the sake of brevity of the disclosure. Further, although there is one flex sensor shown to be positioned on each of the shoulders, it may be contemplated that the number and position of the flex sensors may be varied to achieve similar results without deviating from the scope of the claimed subject matter.

Further, the second posture sensor 204 is configured to monitor a second bend parameter associated with the vertebral column 118 of the user 104. As shown in FIG. 2, the second posture sensor 204 is positioned on the back strap 112 of the harness 100, and accordingly configured to be positioned on the vertebral column 118 and in between the left and the right shoulders 116 of the user 104. In one example, the second posture sensor 204 includes a stretch sensor configured to change resistance according to the stretch detected in the vertebral column 118, thereby indicating the posture of the vertebral column 118 of the user 104. Although only one stretch sensor is shown to be positioned on the vertebral column 118 of the user 104, it may be contemplated that the type, number and position of the second posture sensor 204 may also be varied to achieve similar results without deviating from the scope of the claimed subject matter.

The control unit 206 is configured to compare the first bend parameter received from the first posture sensor 202 with a first predefined reference value to detect an improper bend or curvature in the shoulders 116 of the user 104. Further, the control unit 206 is configured to compare the second bend parameter received from the second posture sensor 204 with a second predefined reference value to detect an improper bend or stretch in the vertebral column 118 of the user 104. For example, a reference curvature in the shoulders 116 and a reference posture of the vertebral column 118 may be used to indicate, to the posture monitoring device 102, that such reference curvature and posture is comfortable and correct for the user 104. Therefore, any deviation (positive or negative) from the reference curvature and posture will be identified as an improper bend or posture by the control unit 206.

In an exemplary embodiment of the present disclosure, the first and the second predefined reference values may be set during an initial calibration of the posture monitoring device 102 specific to the user 104 wearing it. The user 104 may calibrate the posture monitoring device 102 according to the desired comfortable posture. For example, the user 104 may perform calibration using the mobile device 209, by providing feedback on the posture of the shoulders 116 and the vertebral column 118 that are comfortable, regular and normal for the user 104.

Accordingly, for a specific posture of the shoulders 116, when the user 104 indicates it to be a comfortable and correct posture through the mobile device 209, the control unit 206 identifies the measured reading of the first posture sensor 202 and stores the measured readings as the first predefined reference value for future. Similarly, for a specific posture of the vertebral column 118, when the user 104 indicates it to be a comfortable and correct posture through the mobile device 209, the control unit 206 identifies the measured reading of the second posture sensor 204 and stores the measured readings as the second predefined reference value for future.

In an alternative embodiment, the control unit 206 may receive standard posture related guidelines, such as the ones provided by physiotherapists to calibrate the posture monitoring device 102. Therefore, in such implementations, the control unit 206 may identify the first predefined reference value and the second predefined reference value from the standard posture related guidelines. In a yet another implementation, the posture monitoring device 102 may be calibrated using both the user feedback and the standard posture related guidelines together.

During operation, when the user 104 wears the wearable posture monitoring device 102, the first and the second posture sensors 202, 204 measure the bend in the shoulders 116 as well as the vertebral column 118. When the measured bend in shoulders 116 is greater than or less than the first predefined reference value, the control unit 206 detects an improper bend in the shoulders 116. Similarly, when the measured stretch and the determined posture of the vertebral column 118 deviates positively or negatively with respect to the second predefined reference value, the control unit 206 detects the improper bend in the vertebral column 118 of the user 104.

In an embodiment of the present disclosure, the control unit 206 is configured to display a visual indication on a display interface 216 of the I/O unit 208 to indicate the detected improper bend of the shoulders 116 and/or the vertebral column 118 of the user 104. The visual indication may be in the form of a visual alert, a textual alert, or a combination thereof. The visual indication may be configured to indicate to the user 104 that he/she needs to correct the posture of the shoulders 116 and/or the vertebral column 118 to avoid fatigue and injury.

Further, the control unit 206 is configured to monitor the bend and curvature of the shoulders 116 and the vertebral column 118 for a time period T and provide a trend of deviation in the monitored posture (of the shoulders 116 and the vertebral column 118) of the user 104 through the display interface 216. The time period T may correspond to the time when the user 104 wears the wearable posture monitoring device 102, such as during the working hours of a day. However, the time period T may be varied to achieve similar results without deviating from the scope of the claimed subject matter.

Figure 4:
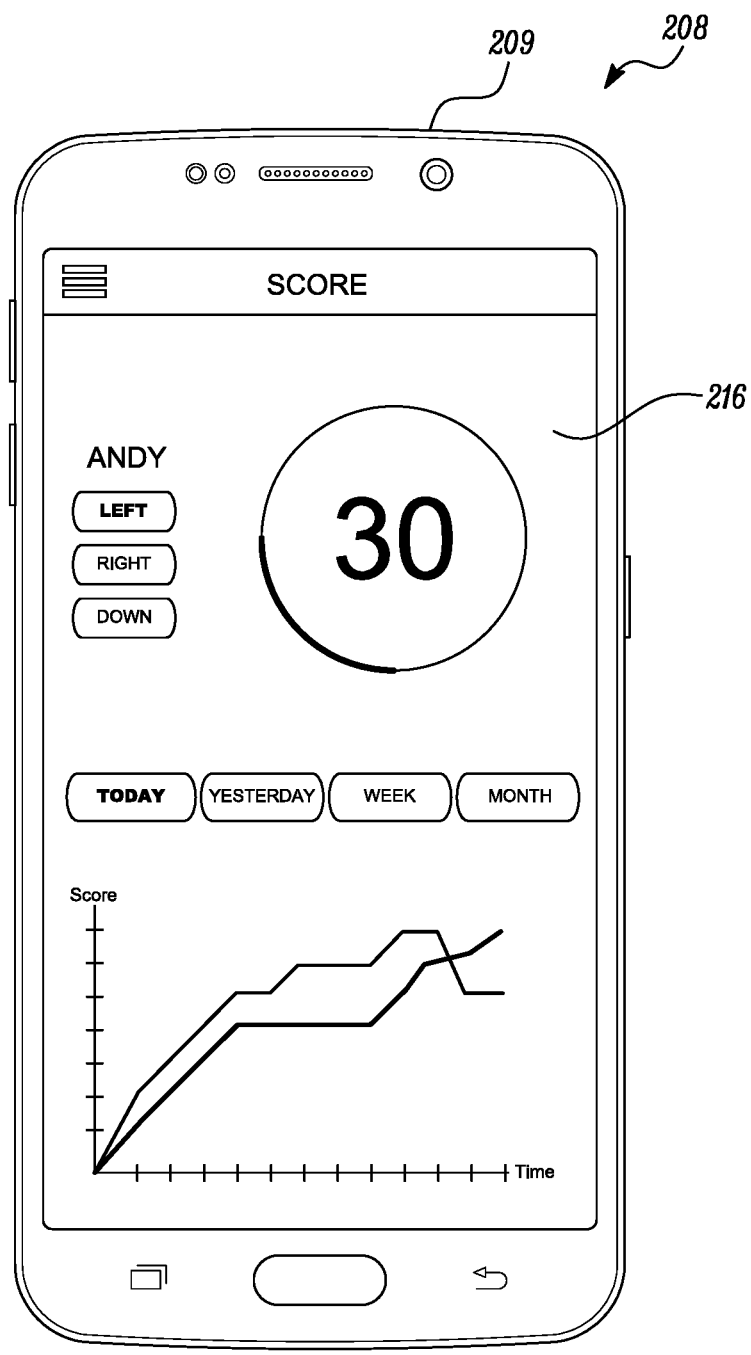
FIG. 4 illustrates an exemplary trend of deviation displayed on a display interface, in accordance with an embodiment of the present disclosure.

For example, the control unit 206 determines a plurality of first bend parameters associated with the shoulder 116 and a plurality of second bend parameters associated with the vertebral column 118 over the time period T. Further, the control unit 206 is configured to compare each of the determined first bend parameters associated with the shoulders 116 with the first predefined reference value to provide a trend of deviation in the curvature of the shoulders 116 throughout the time period T, on the display interface 216 of the I/O unit 208. It may be contemplated that the control unit 206 may also provide the trend of deviation for each of the shoulders 116 separately. Similarly, the control unit 206 is configured to compare each of the determined second bend parameters associated with the vertebral column 118 with the second predefined reference value to provide a trend of deviation in the posture of the vertebral column 118 throughout the time period T, on the display interface 216 of the I/O unit 208. FIG. 4 illustrates an exemplary trend of deviation displayed on the display interface 216 of the I/O unit 208. The user 104 may view the trend of deviation to check the progress of improvement in posture while working during the day.

In an embodiment of the present disclosure, the control unit 206 is operatively coupled to a database 217 to receive one or more posture training exercise information based on the detected improper bend and curvature in one or more of the shoulders 116 and the vertebral column 118 of the user 104. The control unit 206 is further configured to display the one or more posture training exercise information on the display interface 216 of the I/O unit 208.

In some alternative implementations, the processor of the mobile device 209 may receive the information related to the detected improper bend and curvature from the control unit 206 and accordingly communicate with the database 217 to receive the one or more posture training exercise information for display. In such a case, the mobile device 209 may communicate with the database 217 over a network, such as the Internet, Intranet, LAN, WAN or the like. In a yet another embodiment, the control unit 206 may include an in-build memory (not shown) having a number of posture training exercise information stored thereon, and the control unit 206 may extract, from the memory, and display the one or more posture training exercise information based on the detected improper bend in one or more of the shoulders 116 and the vertebral column 118 of the user 104.

Figure 5:
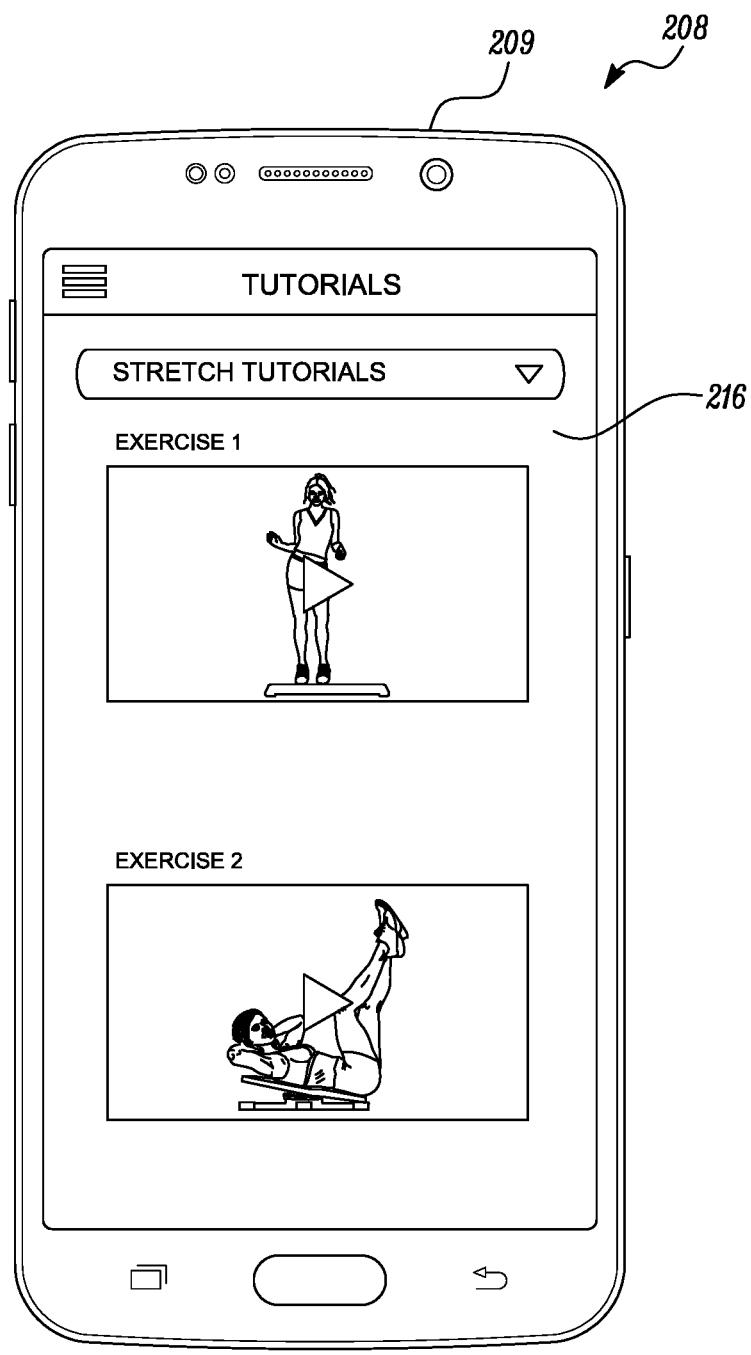
FIG. 5 illustrates the exemplary display interface displaying posture training exercises, in accordance with the embodiment of the present disclosure.

In an embodiment of the present disclosure, the one or more posture training exercise information may be displayed as video tutorials of exercises (as shown in FIG. 5) corresponding to the detected abnormality in the posture of the shoulders 116 and/or the vertebral column 118. For example, if the control unit 206 detects improper bend or curvature in the shoulders 116 for a long time during the time period T, one or more posture training exercises for the shoulders 116 may be displayed on the display interface 216 of the mobile device 209. Similarly, if the control unit 206 detects an improper posture of the vertebral column 118 for a long time, then one or more posture training exercises for the vertebral column 118, such as stretch tutorial exercises, may be displayed on the display interface 216 of the mobile device 209. Although, the one or more posture training exercise information is shown and described to be in the form of video tutorials, it may be contemplated that the same may be provided in any other manner, without deviating from the scope of the claimed subject matter. In some alternative examples, the posture training exercise information may be displayed as step-by-step textual or audio-visual instructions or a combination thereof.

Further, the posture monitoring device 102 may additionally include a feedback unit 218 mounted thereon and configured to provide a feedback to the user 104 every time an incorrect bend in the shoulders 116 and the vertebral column 118 is detected. The feedback unit 218 may include a haptic sensor, such as a vibrator, configured to vibrate when the improper bend in the shoulders 116 and/or the vertebral column 118 is detected. In an exemplary embodiment, the feedback unit 218 may be configured to continuously vibrate until the user 104 corrects the posture. In an alternative implementation, the feedback unit 218 may intermittently vibrate to indicate the abnormal posture and/or bend to the user 104.

Although the posture monitoring device 102 of the present disclosure, is described and shown to include sensors on the shoulders and the back/vertebral column of the user, it may be contemplated that the number and position of the sensors may be varied to achieve similar results without deviating from the scope of the claimed subject matter.

INDUSTRIAL APPLICABILITY

Figure 6:
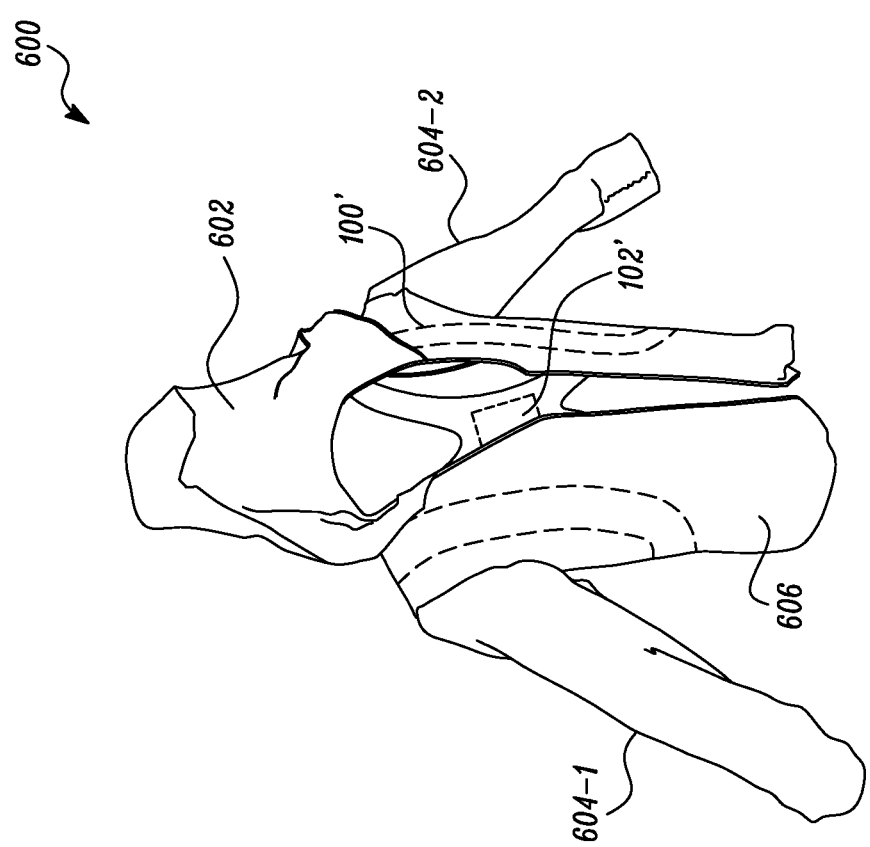
FIGS. 6 & 7 illustrate an exemplary modular jacket having the wearable harness with the wearable posture monitoring device, in accordance with the embodiments of the present disclosure.
Figure 7:
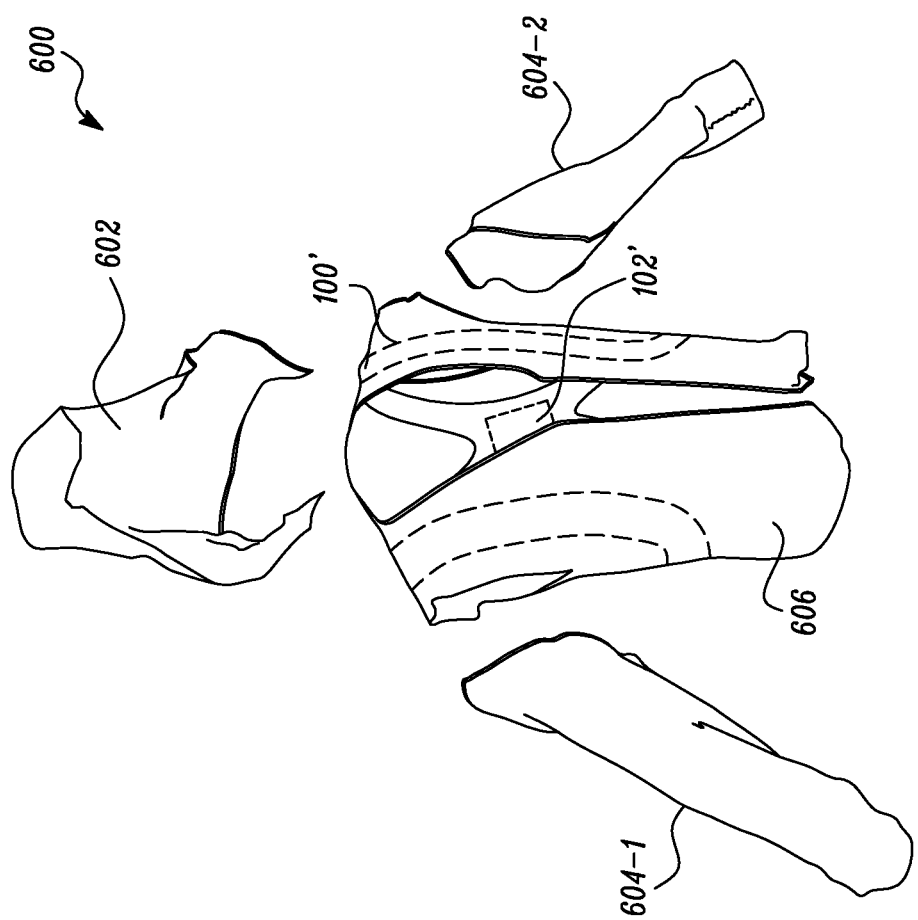

In an exemplary implementation of the present disclosure, the wearable harness 100 and the wearable posture monitoring device 102 of the present disclosure, may be integrated with a wearable garment, such as a jacket 600 shown in FIGS. 6 and 7. In various implementations of the present disclosure, the jacket 600 may be a modular jacket having a removable hood 602, removable sleeves 604, a vest 606 and a removable harness, such as the harness 100' having the wearable posture monitoring device 102'.

In an exemplary embodiment of the present disclosure, the modular jacket 600 includes a connection port (not shown), such as a USB (Universal Serial Bus) connection port to facilitate connection of the removable harness 100' and the wearable posture monitoring device 102' to the jacket 600. Therefore, a user 104 may wear the entire modular jacket 600 including the harness 100' and the wearable posture monitoring device 102' during working hours to monitor posture through out the work day. Alternatively, the user 104 may detach the components of the jacket 600 as desired according to their specific requirements. For example, in summers, the workers may detach the hood 602 and the sleeves 604 and wear only the vest 606 along with the harness 100' and the wearable posture monitoring device 102'. Similarly, during winter season, the user 104 may attach the hood 602, the sleeves 604 to the vest 606 and the harness 100' having the wearable posture monitoring device 102'.

In some other implementations, the user 104 may wear only the wearable harness 100, 100' having the posture monitoring device 102, 102' to monitor posture related information associated with the shoulders 116 and the vertebral column 118 of the user 104 throughout the working day. In such cases, the user 104 may wear the wearable harness 100, 100' having the posture monitoring device 102, 102' with their existing apparels to avoid any extra expense of buying a new apparel with an integrated wearable posture monitoring device 102, 102'.

In an exemplary embodiment of the present disclosure, the display interface 216 may be implemented in the form of an application for the mobile device 209, where the user 104 may login using login credentials to view the information and data captured by the wearable posture monitoring device 102, as described in the foregoing description.

The wearable posture monitoring device 102 of the present disclosure, may be useful for people who have jobs involving physical work where the improper posture may result in fatigue and reduced efficiency and productivity. The user 104 wearing the posture monitoring device 102 may be able to monitor their posture throughout the day and also see trends of deviation to monitor their progress of improvement.

Figure 8:
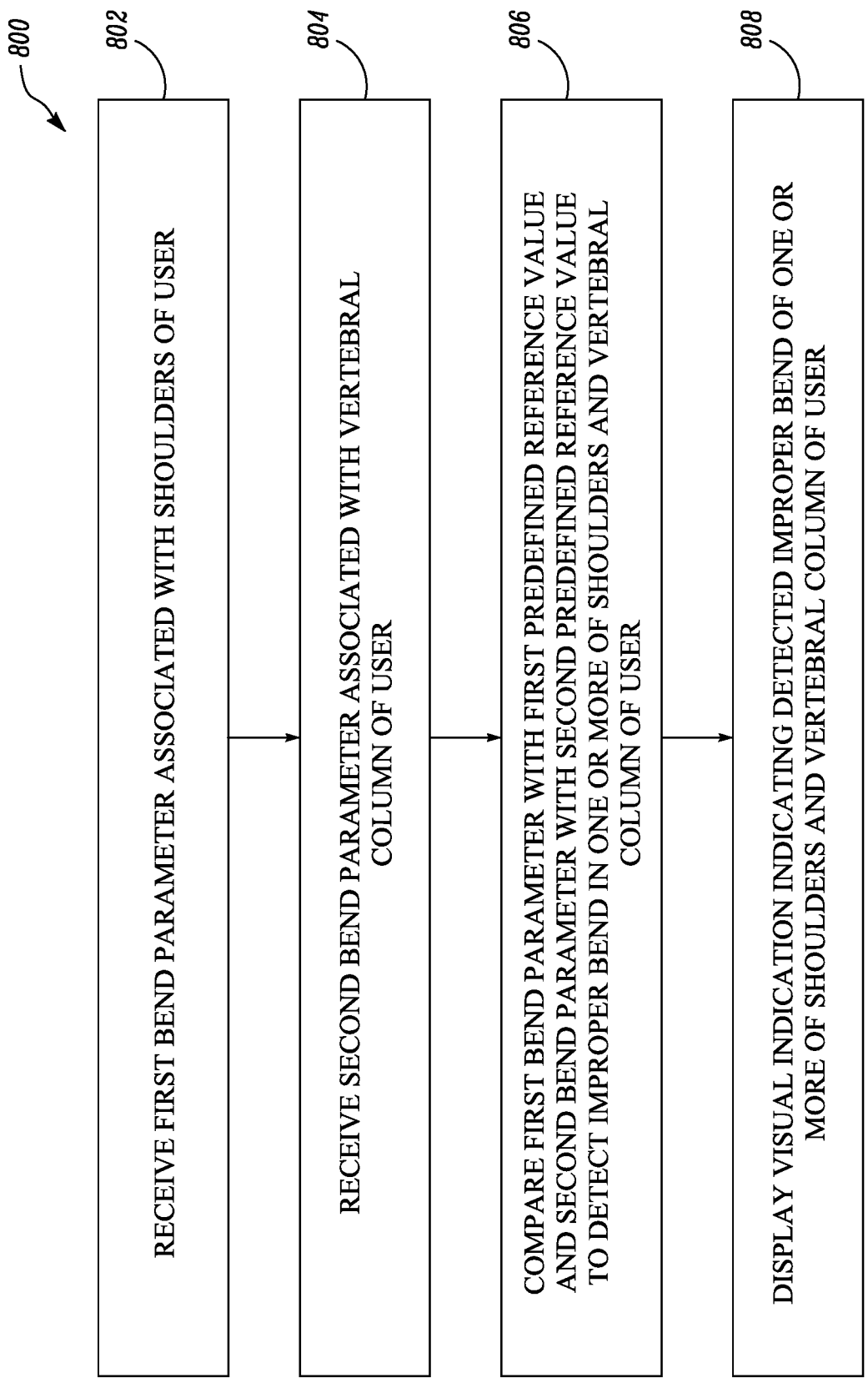
FIG. 8 illustrates an exemplary method flowchart for monitoring posture of the user, in accordance with an embodiment of the present disclosure.

FIG. 8 illustrates an exemplary method 800 for monitoring posture of a user 104 wearing the wearable harness 100 having the wearable posture monitoring device 102, according to the various embodiments of the present disclosure.

When the user 104 wears the harness 100 having the wearable posture monitoring device 102, the control unit 106 provided on the wearable posture monitoring device 102 performs the following steps for monitoring the posture related information associated with the shoulders 116 and the vertebral column 118 of the user 104.

Initially, at step 802, the control unit 206 receives a first bend parameter associated with the shoulders 116 from the one or more first posture sensor 202 mounted on the wearable posture monitoring device 102. The first bend parameter may indicate the bend or curvature in the shoulders 116 of the user 104. For example, the first flex sensor 210 and the second flex sensor 212 positioned on each of the shoulders 116 may be configured to determine the bend and curvature in the shoulder 116 of the user 104.

At step 804, the control unit 206 receives the second bend parameter associated with the vertebral column 118 from the one or more second posture sensor 204 mounted on the wearable posture monitoring device 102. The second bend parameter may indicate the posture of the vertebral column of the user 104. For example, the stretch sensor positioned on the vertebral column 118 of the user 104 and is configured to change resistance based on the stretch in the vertebral column 118.

At step 806, the control unit 206 compares the received first bend parameter with a first predefined reference value and the received second bend parameter with a second predefined reference value to detect an improper bend in one or more of the shoulders 116 and the vertebral column 118 of the user 104. In an exemplary embodiment of the present disclosure, the first and the second predefined reference values may be set during an initial calibration of the posture monitoring device 102 specific to the user 104 wearing it. The user 104 may calibrate the posture monitoring device 102 according to the desired comfortable posture.

At step 808, the control unit 206 displays a visual indication indicating the detected improper bend of the one or more of the shoulders 116 and vertebral column 118 of the user 104. In an exemplary embodiment, the control unit 206 displays the visual indication on the display interface 216 of the I/O unit 208 to indicate the detected improper bend of the shoulders 116 and/or the vertebral column 118 of the user 104. The visual indication may be in the form of a visual alert, a textual alert, or a combination thereof.

Further, the control unit 206 monitors the bend and curvature of the shoulders 116 and the vertebral column 118 for a time period T to provide and display a trend of monitored posture to the user 104 through the display interface 216. For example, the control unit 206 receives a plurality of first bend parameters associated with the shoulder 116 and a plurality of second bend parameters associated with the vertebral column 118 over the time period T. The control unit 206 further compares each of the determined first bend parameters associated with the shoulders 116 with the first predefined reference value and each of the second bend parameters associated with the vertebral column 118 to provide a trend of deviation in the curvature of the shoulders 116 and/or the vertebral column 118 throughout the time period T, on the display interface 216 of the I/O unit 208.

In a further embodiment of the present disclosure, the control unit 206 is further configured to display one or more posture training exercise information on the display interface 216 of the I/O unit 208 based on the detected abnormal and improper bend in one or more of the shoulders 116 and the vertebral column 118 of the user 104. For example, if the control unit 206 detects improper bend or curvature in the shoulders 116 for a long time, one or more posture training exercises for the shoulders 116 may be displayed on the display interface 216, whereas, if the control unit 206 detects an improper posture of the vertebral column 118 for a long time, then one or more posture training exercises for the vertebral column 118, such as stretch tutorial exercises, may be displayed on the display interface 216 of the mobile device 209.

Furthermore, the control unit 206 may provide an alert to the user 104, in the form of a haptic feedback, such as vibration, using the feedback unit 218, every time an improper bend and curvature in one or more of the shoulders 116 and the vertebral column 118 is detected.

It will be apparent to those skilled in the art that various modifications and variations can be made to the system of the present disclosure without departing from the scope of the disclosure. Other embodiments will be apparent to those skilled in the art from consideration of the specification and practice of the system disclosed herein. It is intended that the specification and examples be considered as exemplary only, with a true scope of the disclosure being indicated by the following claims and their equivalent.

What is claimed is:

1. A wearable posture monitoring device comprising:
   a first posture flex sensor positioned on a first shoulder strap of a harness forming a loop around a left shoulder of a user and a second posture flex sensor positioned on a second shoulder strap of the harness forming a loop around a right shoulder of the user to measure a first bend parameter associated with left and right shoulders of a user;
   at least one posture stretch sensor configured to change resistance according to an amount of stretch detected in a vertebral column to measure a second bend parameter associated with the vertebral column of the user, arranged in a V-shaped configuration with the first posture flex sensor and the second posture flex sensor such that the three sensors are generally coplanar;
   a control unit operatively coupled to the first posture flex sensor, the second posture flex sensor, and the at least one posture stretch sensor, the control unit being configured to:
      compare the first bend parameter with a first predefined reference value and the second bend parameter with a second predefined reference value to detect an improper bend in the left and right shoulders and in the vertebral column of the user; and
   display a visual indication, on a display interface associated with the posture monitoring device, to indicate the detected improper bend of one or more of the shoulders and vertebral column of the user.

2. The wearable posture monitoring device of claim 1, wherein the first predefined reference value and the second predefined reference value are set during an initial calibration of the wearable posture monitoring device by the user.

3. The wearable posture monitoring device of claim 1, wherein the first posture flex sensor is configured to be positioned on the left shoulder of the user and the second posture flex sensor is configured to be positioned on the right shoulder of the user.

4. The wearable posture monitoring device of claim 1, wherein the control unit is further configured to:
   determine a plurality of first bend parameters and second bend parameters within a time period;
   compare each of the plurality of first bend parameters with the first predefined reference value and each of the second bend parameters with the second predefined reference value to determine a trend of deviation in the first bend parameters and second bend parameters with respect to the respective reference values for the time period; and
   display, on the display interface associated with the wearable posture monitoring device, the determined trend of deviation for the time period.

5. The wearable posture monitoring device of claim 1, wherein the control unit is operatively coupled to a database, the control unit being further configured to:
   receive one or more posture training exercise information from the database, based on the detected improper bend in one or more of the shoulders and vertebral column of the user; and
   display, on the display interface associated with the wearable posture monitoring device, the one or more posture training exercise information received from the database.

6. The wearable posture monitoring device of claim 1 further comprising a feedback unit coupled to the control unit and configured to provide an alert to the user when an improper bend of the one or more of shoulders and the vertebral column is detected.

7. The wearable posture monitoring device of claim 6, wherein the alert is one or more of a visual alert, a textual alert, haptic feedback, or combination thereof.

8. A wearable harness including the wearable posture monitoring device of claim 1, wherein the wearable harness comprises:
   a pair of shoulder straps having the one or more first posture sensor mounted thereon; and a back strap having the one or more second posture sensor mounted thereon.

9. The device of claim 1, wherein the control unit does not receive an input from a gyroscope or an accelerometer to detect the improper bend in the left and right shoulders and in the vertebral column of the user.

* * * * *